(12) United States Patent
Hardert et al.

(10) Patent No.: US 9,987,461 B2
(45) Date of Patent: Jun. 5, 2018

(54) HEMODIALYSIS CATHETER WITH THROMBUS BLOCKER

(75) Inventors: Michael W. Hardert, Bloomington, IN (US); Michael R. Kurrus, Ellettsville, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 74 days.

(21) Appl. No.: 12/903,677

(22) Filed: Oct. 13, 2010

(65) Prior Publication Data

US 2012/0095416 A1   Apr. 19, 2012

(51) Int. Cl.
*A61M 25/00* (2006.01)
*A61M 1/36* (2006.01)

(52) U.S. Cl.
CPC ...... *A61M 25/0026* (2013.01); *A61M 1/3661* (2014.02)

(58) Field of Classification Search
CPC .. A61B 17/221; A61F 2/013; A61F 2002/016; A61F 2/01; A61F 2002/011; A61F 2230/0006; A61F 2230/0078; A61F 2230/008
USPC ..... 604/626, 265, 266, 267, 93.01; 128/899; 606/200
See application file for complete search history.

(56) References Cited

U.S. PATENT DOCUMENTS

| | | | | | |
|---|---|---|---|---|---|
| 3,472,230 | A | * | 10/1969 | Fogarty ............... | A61B 17/221 606/127 |
| 3,952,747 | A | * | 4/1976 | Kimmell, Jr. ............ | A61F 2/01 128/899 |
| 4,425,908 | A | * | 1/1984 | Simon ..................... | A61F 2/01 128/899 |
| 4,619,246 | A | * | 10/1986 | Molgaard-Nielsen .... | A61F 2/01 128/899 |

(Continued)

FOREIGN PATENT DOCUMENTS

DE  33 26 648 A1  2/1985
EP  1 681 073 B1  8/2007

OTHER PUBLICATIONS

Hoperoft et al. What is the Young's Modulus of Silicon? Journal of Microelectric Systems, col. 19, No. 2, 2010.*

(Continued)

*Primary Examiner* — Bhisma Mehta
*Assistant Examiner* — Matthew A Engel
(74) *Attorney, Agent, or Firm* — Brinks Gilson & Lione

(57) ABSTRACT

A hemodialysis catheter with a plurality of umbrella-like wire members covered with a film which works as a thrombus blocker and can easily and effectively remove the thrombus is disclosed. The hemodialysis catheter has a proximal lumen, the arterial lumen, and a distal lumen, the venous lumen. An elongate member is longitudinally put in either the proximal lumen or the distal lumen, or two elongate members in both lumens. A plurality of umbrella-like wire members are connected to the end of the elongate (Continued)

member. When the hemodialysis catheter is put in the vessel but not in use, the end of the lumen is capped off by the plurality of umbrella-like wire members covered with a film. When it is ready to use, the doctor can pull the elongate member which connects to the plurality of umbrella-like wire members out off the lumen inverting the plurality of umbrella-like wire members and clearing away any thrombus that has formed.

22 Claims, 2 Drawing Sheets

(56) References Cited

U.S. PATENT DOCUMENTS

| | | | | |
|---|---|---|---|---|
| 4,643,184 | A * | 2/1987 | Mobin-Uddin | A61F 2/01 606/198 |
| 4,723,549 | A * | 2/1988 | Wholey | A61F 2/013 604/913 |
| 4,727,873 | A * | 3/1988 | Mobin-Uddin | A61F 2/01 606/200 |
| 4,790,812 | A * | 12/1988 | Hawkins et al. | 604/22 |
| 4,832,055 | A * | 5/1989 | Palestrant | A61F 2/01 128/899 |
| 4,873,978 | A * | 10/1989 | Ginsburg | A61F 2/013 606/198 |
| 5,011,488 | A * | 4/1991 | Ginsburg | 606/159 |
| 5,041,093 | A * | 8/1991 | Chu | 604/104 |
| 5,071,407 | A * | 12/1991 | Termin et al. | 604/104 |
| 5,324,304 | A * | 6/1994 | Rasmussen | A61F 2/01 128/899 |
| 5,509,900 | A * | 4/1996 | Kirkman | 604/104 |
| 5,549,626 | A * | 8/1996 | Miller | A61F 2/01 606/191 |
| 5,591,195 | A * | 1/1997 | Taheri | A61B 17/1219 606/191 |
| 5,649,953 | A * | 7/1997 | Lefebvre | A61F 2/01 604/104 |
| 5,669,933 | A * | 9/1997 | Simon | A61F 2/01 600/191 |
| 5,935,139 | A * | 8/1999 | Bates | 606/159 |
| 6,371,969 | B1 * | 4/2002 | Tsugita | A61F 2/01 606/200 |
| 6,383,174 | B1 * | 5/2002 | Eder | A61B 17/12022 606/1 |
| 6,544,278 | B1 * | 4/2003 | Vrba | A61F 2/01 606/192 |
| 6,592,546 | B1 * | 7/2003 | Barbut | A61B 17/12022 604/104 |
| 7,326,196 | B2 * | 2/2008 | Olsen et al. | 604/523 |
| 8,152,831 | B2 * | 4/2012 | Magnuson | A61F 2/013 606/200 |
| 8,182,508 | B2 * | 5/2012 | Magnuson | A61F 2/013 606/200 |
| 8,187,298 | B2 * | 5/2012 | Pal | A61F 2/013 606/200 |
| 8,216,269 | B2 * | 7/2012 | Magnuson | A61F 2/013 606/200 |
| 8,221,446 | B2 * | 7/2012 | Pal | A61F 2/013 606/191 |
| 8,377,092 | B2 * | 2/2013 | Magnuson | A61F 2/013 606/200 |
| 8,795,322 | B2 * | 8/2014 | Cully | A61F 2/013 606/200 |
| 8,945,169 | B2 * | 2/2015 | Pal | 606/192 |
| 2003/0163158 | A1 * | 8/2003 | White | A61B 17/22032 606/200 |
| 2005/0196421 | A1 * | 9/2005 | Hunter et al. | 424/423 |
| 2007/0112374 | A1 * | 5/2007 | Paul, Jr. | A61F 2/013 606/200 |
| 2007/0197962 | A1 * | 8/2007 | Morikawa | 604/96.01 |

OTHER PUBLICATIONS

About—Merriam Webster Dictionary, accessed online Aug. 19, 2014.*

Notification of Transmittal of the International Search Report and the Written Opinion of the International Searching Authority, or the Declaration, dated Dec. 14, 2011, for PCT/US2011/054533, 6 p.

* cited by examiner

HEMODIALYSIS CATHETER WITH THROMBUS BLOCKER

FIELD OF THE INVENTION

The present invention is related generally to a hemodialysis catheter and more particularly to a catheter with thrombus blocker adapted for hemodialysis.

BACKGROUND OF THE INVENTION

A treatment of a number of medical conditions requires the placement of catheters in a patient's blood vessel for an extended period time. These long-term applications include blood access for hemodialysis, chemotherapy, parental nutrition, blood transfusions and blood sampling.

It is well known in the medical field that chronic placement of a catheter in a patient's blood vessel often results in catheter failure due to many reasons. Thrombus formation at the tip of the catheter is one of the reasons. According to many medical journal articles, thrombus formation at the tip of the catheter is related to the structural design of a catheter.

Current hemodialysis catheters are used to filter blood in the superior vena cava (SVC). Typically, they have two lumens. One is the arterial lumen which is used to aspirate blood which travels to the dialysis machine; another is the venous lumen which ejects the filtered blood into the SVC and then heart and lungs, and the rest of the body. Traditionally the arterial lumen is always the proximal lumen and the venous lumen is always the distal lumen. This is done to prevent recirculation, where previously filtered and newly ejected blood is sucked back in and re-filtered by the machine. Depending on the tip design, the vacuum created at the proximal arterial opening can sometimes draw the catheter against the SVC wall, thereby occluding the opening, lowering the flow rate, and preventing dialysis from taking place. Accordingly, many hemodialysis catheters provide the proximal lumen with one or more additional side ports to mitigate occlusion of the proximal opening.

To prevent thrombus from forming inside the catheter between uses, a so-called heparin lock is used where the catheter is flushed with heparin and clamped off so that the normal inside volume of the catheter is occupied by heparin. However, side ports on the proximal lumen of the catheter can prevent the effectiveness of heparin or other anticoagulants because heparin can leak out of the sideports leaving catheter shaft distal to the sideports unprotected. Many medical articles point to hemodialysis side ports as being a cause for thrombus and fibrous sheath formation, this lowers blood flow rates and makes the catheter non-functional.

Accordingly, it is desired to provide a catheter with thrombus blocker that can easily and effectively remove and/or prevent the thrombus forming at the tip of the catheter.

SUMMARY OF THE INVENTION

This invention provides a hemodialysis catheter with a plurality of umbrella-like wire members which work as a thrombus blocker and can easily and effectively remove thrombus formation and prevent thrombus formation on the catheter shaft.

The hemodialysis catheter has two lumens. The catheter may have a third lumen. The first lumen is the arterial lumen and has a distal end which aspirates blood which travels to the dialysis machine. The second lumen is the venous lumen, which is adjacent with said first lumen, and has a distal end which ejects the filtered blood into the SVC and then heart and lungs, and the rest of the body. The arterial lumen is the proximal lumen and the venous lumen is the distal lumen. One elongate member is longitudinally placed in said first lumen and has a distal end. The distal end of the elongate member is connected with a plurality of umbrella-like wire members.

When the hemodialysis catheter is placed in the vessel but not in use, the distal end of the proximal and/or distal lumen is capped off by the plurality of umbrella-like wire members. When the hemodialysis catheter is ready to use, the doctor, technician or nurse can pull the elongate member which connects with the plurality of umbrella-like wire members out of the lumen to invert the plurality of umbrella-like wire members and clear away or capture any thrombus that has formed at the proximal end of the arterial lumen or at the distal end of the venous lumen. The plurality of umbrella-like wire members comprises nitinol. A film is mounted on the plurality of umbrella-like wire members by means of molding or suture. The film may be elastic or inelastic.

In another embodiment, all structures of the hemodialysis catheter remain same as the previous embodiment except the elongate member which has a distal end and connects with a plurality of umbrella-like wire members is longitudinally placed in said second lumen instead of the first lumen.

If desired, two elongate members can be separately placed into the two lumens and separately connected with the plurality of umbrella-like wire members. Both ends of the arterial lumen and venous lumen are separately capped off by the plurality of umbrella-like wire members when the hemodialysis catheter is put in the vessel but not in use.

Where the arterial lumen and venous lumen are used separately, the hemodialysis catheter has only one lumen. The plurality of umbrella-like wire members covers the end of the lumen when the hemodialysis catheter is put in the vessel but not in use.

DETAILED DESCRIPTION OF THE INVENTION

Figure 1:
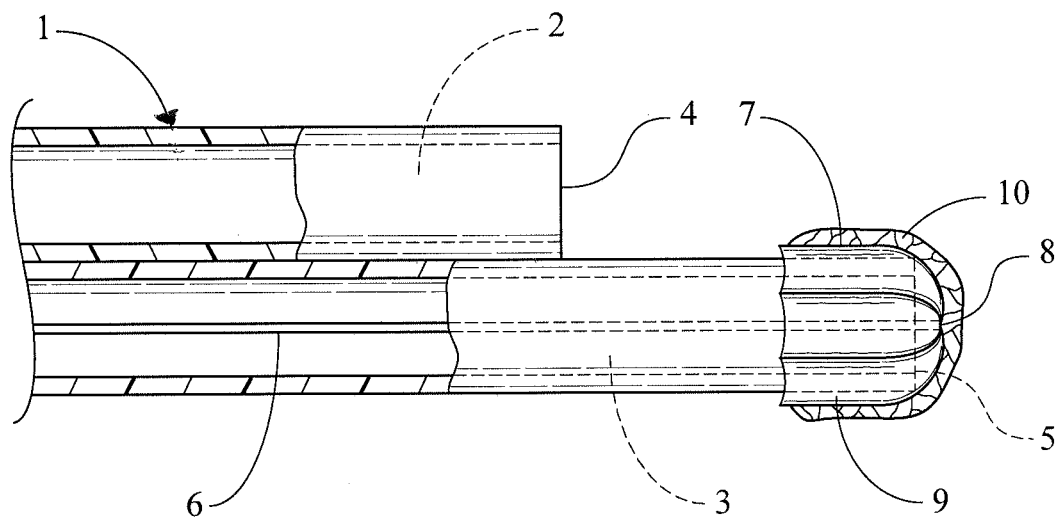
FIG. 1 is a side view of a first preferred embodiment of the hemodialysis catheter with two lumens.

FIG. 1 illustrates a presently preferred embodiment. The hemodialysis catheter has a hemodialysis catheter elongate shaft 1 having two lumens 2 and 3. The first lumen is the proximal lumen 2, the arterial lumen, which can aspirate blood which travels to the dialysis machine. The proximal lumen 2 has a distal end 4. The second lumen is the distal lumen 3, the venous lumen, which can eject the filtered blood into the SVC and then heart and lungs, and the rest of the body. The distal lumen 3 has a distal end 5.

Figure 2:
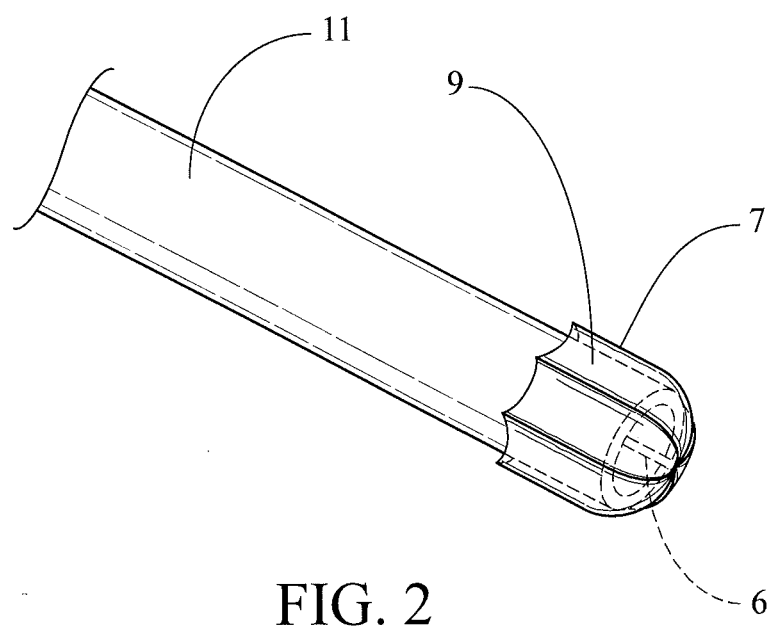
FIG. 2 shows, in a perspective view, the plurality of umbrella-like wire members covering the end of the lumen.
Figure 4:
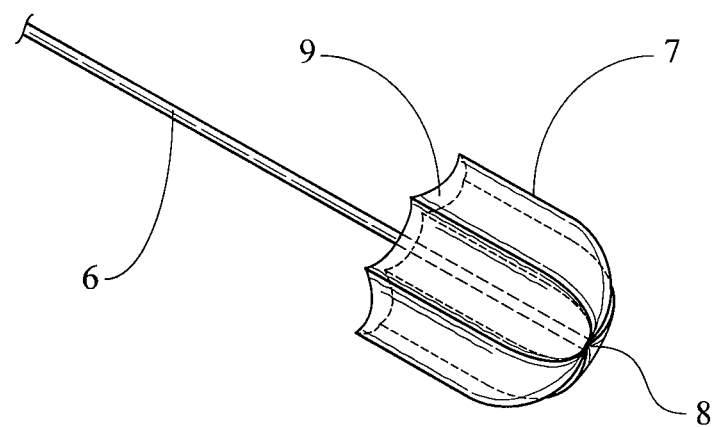
FIG. 4 is a perspective view of the elongate member with the plurality of umbrella-like wire members.

Referring FIG. 1, FIG. 2 and FIG. 4, an elongate member 6 is longitudinally disposed in the distal lumen 3. The elongate member 6 has a distal end 8. A plurality of umbrella-like wire members 7 are connected to the distal end 8 of the elongate member 6. A film 9 is mounted on the plurality of umbrella-like wire members 7. When the elongate shaft 1 is placed in the vessel but not in use, the distal end 5 of the distal lumen 3 is capped off by the plurality of umbrella-like wire members 7. When it is ready to use, the doctor can pull the plurality of umbrella-like wire members 7 out of the distal lumen 3 inverting the plurality of umbrella-like wire members 7 and clear away any thrombus 10 that has formed.

Figure 3:
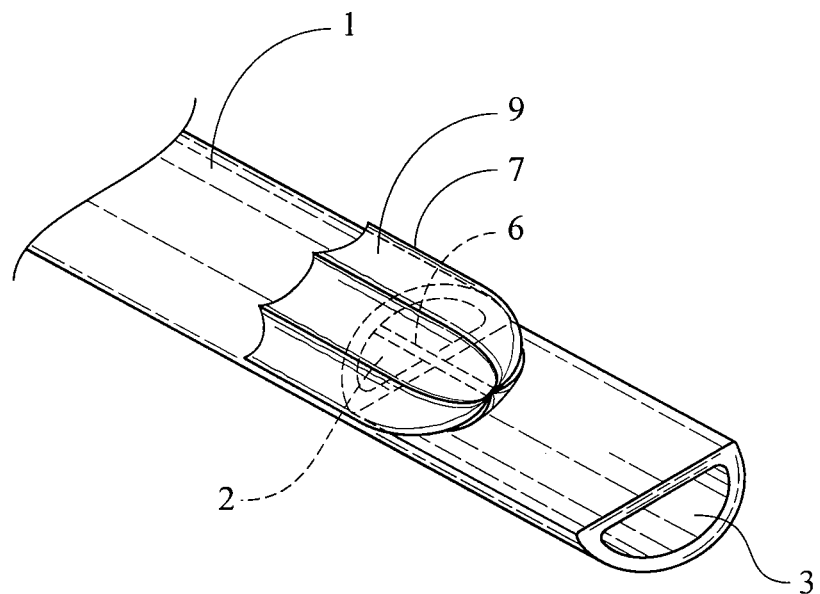
FIG. 3 is a perspective view of a second preferred embodiment of the hemodialysis catheter with two lumens.

FIG. 3 illustrates the second embodiment. This hemodialysis catheter also has a hemodialysis catheter elongate shaft 1 having two lumens 2 and 3. The structure and the feature of each lumen are the same as the first embodiment. The first lumen is the proximal lumen 2, the arterial lumen, which can aspirate blood which travels to the machine. The second lumen is the distal lumen 3, the venous lumen, which can eject the filtered blood into the SVC and then heart and lungs, and the rest of the body.

An elongate member 6 is longitudinally disposed in the proximal lumen 2 (instead of the distal lumen 3 as shown in FIG. 1.) A plurality of umbrella-like wire members 7 are connected to the elongate member 6. A film 9 is mounted on the plurality of umbrella-like wire members 7. When the elongate shaft 1 is put in the vessel but not in use, the proximal lumen 2 is capped off by the plurality of umbrella-like wire members 7. When it is ready to use, the doctor can pull the plurality of umbrella-like wire members 7 out of the proximal lumen 2 inverting the plurality of umbrella-like wire members 7 and clear away any thrombus that has formed.

FIG. 2 shows the last embodiment. The hemodialysis catheter 11 has only one lumen. An elongate member 6 is longitudinally disposed in the lumen. A plurality of umbrella-like wire members 7 covers the end of the lumen.

We claim:

1. A hemodialysis catheter with thrombus blocker comprising:
   an elongate shaft extending from a proximal end portion to a distal end portion;
   a first lumen extending through the shaft and having a distal end;
   a second lumen extending through the shaft and having a distal end, said second lumen being disposed adjacent to said first lumen;
   an elongate member longitudinally and removably disposed in one of said first or second lumens; and
   a plurality of curvilinear umbrella-like wire members each extending between a first end and a second end, said first end being connected to a distal end of said elongate member and said second end being proximal of and spaced apart from the distal end of said elongate member, said plurality of curvilinear umbrella-like wire members forming an umbrella-like structure with the second ends of said plurality of curvilinear umbrella-like members circumferentially disposed about and fully encompassing an outer circumference of the distal end portion of said shaft, said second ends being disposed proximally of circumferentially about the distal end portion of said shaft so as to encompass the distal end portion of said shaft, wherein the plurality of curvilinear umbrella-like wire members each comprise a wire portion extending distally from the second end and towards the distal end of the elongate member, wherein the wire portions are each spaced apart from each other in a parallel non-contacting manner, and are disposed externally to and proximally of the distal end of the elongate member so as to circumferentially encompass the distal end portion of said shaft, wherein the plurality of curvilinear umbrella-like wire members are configured to be inverted and movably disposed within said first or second lumen so as to permit removal of the elongate member from the proximal end portion of the shaft, and wherein the umbrella-like structure is configured to inhibit or remove thrombus formation from about the outer circumference of the distal end portion of said shaft upon rotation of the elongate member relative to the shaft.

2. A hemodialysis catheter with thrombus blocker as claim 1, wherein the elongate member is longitudinally placed in said first lumen.

3. A hemodialysis catheter with thrombus blocker as claim 2, wherein said plurality of curvilinear umbrella-like wire members of the umbrella-like structure are self-supporting and configured to engage an outer surface of the distal end of said shaft.

4. A hemodialysis catheter with thrombus blocker as claim 3, wherein said plurality of curvilinear umbrella-like wire members are invertable to permit the elongate member to be pulled out of a proximal end of said lumen.

5. A hemodialysis catheter with thrombus blocker as claim 4, wherein said elongate member is made of metal.

6. A hemodialysis catheter with thrombus blocker as claim 5, wherein said plurality of curvilinear umbrella-like wire members comprise nitinol.

7. A hemodialysis catheter with thrombus blocker as claim 6, wherein said plurality of curvilinear umbrella-like wire members are each bonded onto the distal end of said elongate member.

8. A hemodialysis catheter with thrombus blocker as claim 7, wherein said plurality of curvilinear umbrella-like wire members are each welded onto the distal end of said elongate member.

9. A hemodialysis catheter with thrombus blocker as claim 8, wherein a film is mounted about and to said plurality of curvilinear umbrella-like wire members.

10. A hemodialysis catheter with thrombus blocker as claim 9, wherein said film is formed by an over molding process.

11. A hemodialysis catheter with thrombus blocker as claim 10, wherein said film is attached by means of suture.

12. A hemodialysis catheter with thrombus blocker as claim 1, wherein the elongate member is longitudinally placed in said second lumen.

13. A hemodialysis catheter with thrombus blocker as claim 12, wherein said plurality of curvilinear umbrella-like wire members of the umbrella-like structure are self-supporting and configured to engage an outer surface of the distal end of said shaft.

14. A hemodialysis catheter with thrombus blocker as claim 13, wherein said plurality of curvilinear umbrella-like wire members are invertable to permit said elongate member to be pulled out of a proximal end of said lumen.

15. A hemodialysis catheter with thrombus blocker as claim 14, wherein said elongate member is made of metal.

16. A hemodialysis catheter with thrombus blocker as claim 15, wherein said plurality curvilinear umbrella-like wire members comprise nitinol.

17. A hemodialysis catheter with thrombus blocker as claim 16, wherein said plurality of curvilinear umbrella-like wire members are each bonded onto the distal end of said elongate member.

18. A hemodialysis catheter with thrombus blocker as claim 17, wherein said plurality of curvilinear umbrella-like wire members are each welded onto the distal end of said elongate member.

19. A hemodialysis catheter with thrombus blocker as claim 18, wherein a film is mounted about and to said plurality of curvilinear umbrella-like wire members.

20. A hemodialysis catheter with thrombus blocker as claim 19, wherein a film is formed by an over molding process.

21. A hemodialysis catheter with thrombus blocker as claim 20, wherein said film is attached by means of suture.

22. A hemodialysis catheter with thrombus blocker comprising:
   an elongate shaft extending between a proximal end and a distal end;
   a first lumen extending through the shaft and having a first distal opening disposed adjacent to the distal end of the shaft;
   a second lumen extending through the shaft and having a second distal opening disposed proximally of and spaced apart from the first distal opening, said second lumen being disposed adjacent to said first lumen;
   an elongate member longitudinally and removably disposed in one of said first or second lumens;
   a plurality of individual self-supporting umbrella-like wire members connected to and extending radially outwardly and proximally from a distal end of said elongate member, the plurality of individual self-supporting umbrella-like members being disposed in a non-contacting manner along a majority of a length thereof, the majority of the length of the plurality of individual self-supporting umbrella-like wire members being disposed proximally of one of the first or second distal openings, wherein said plurality of individual self-supporting umbrella-like wire members form an umbrella-like structure configured to cap off the first distal opening, and wherein the plurality of individual self-supporting umbrella-like wire members are configured to be inverted and movably disposed within said first or second lumen so as to permit removal of the elongate member from the proximal end of the shaft; and
   a film mounted to said plurality of individual self-supporting umbrella-like wire members, said film extending between adjacent pairs of individual self-supporting umbrella-like wire members of said plurality of individual self-supporting umbrella-like wire members, said film disposed circumferentially about and fully encompassing the distal end of said shaft.

\* \* \* \* \*